United States Patent [19]

Weisman

[11] 4,360,009

[45] Nov. 23, 1982

[54] MEDICAL TREATMENT TABLE

[76] Inventor: Eric Weisman, 2092 E. 11th Ave., North St. Paul, Minn. 55109

[21] Appl. No.: 166,247

[22] Filed: Jul. 7, 1980

[51] Int. Cl.³ .......... A61F 5/00

[52] U.S. Cl. .......... 128/71

[58] Field of Search .......... 128/68.1, 70, 69, 71, 128/72, 74, 75; 273/73; 269/328

[56] References Cited

U.S. PATENT DOCUMENTS

| | | | |
|---|---|---|---|
| 896,114 | 8/1908 | Jacobsen | 128/71 |
| 1,648,631 | 11/1927 | Austin | 128/68.1 |
| 1,740,906 | 6/1929 | Rothauszky | 128/68 |
| 2,723,663 | 11/1955 | Davis | 128/75 |
| 3,081,085 | 3/1963 | Girolamo | 128/68 |
| 4,157,088 | 6/1979 | Gracey | 128/70 |
| 4,181,125 | 1/1980 | Carlson | 128/75 |

*Primary Examiner*—Richard C. Pinkham
*Assistant Examiner*—Carl Moy
*Attorney, Agent, or Firm*—Hugh D. Jaeger

[57] ABSTRACT

Medical treatment table having one degree of freedom and including slidable foot-ankle harnesses for securing a patient's legs to one end of the table. The foot-ankle harnesses slidably move on one end of the table either manually or electrically. The table is tilted by way of an electric motor or a manual override crank. A cervical traction harness at the other end of the table can also be used in conjunction with the table. The table is for the treatment of medical conditions or disorders predetermined by doctors.

10 Claims, 4 Drawing Figures

MEDICAL TREATMENT TABLE

BACKGROUND OF THE INVENTION

1. Field of the Invention

The present invention pertains to medical apparatus, and, more particularly, pertains to a medical treatment table.

2. Description of Prior Art

Prior art medical treatment tables have usually required traction comprising cords connected between the body and weights over a pulley. This type of arrangement has been less than satisfactory, especially for treating disorders such as scoliosis.

The present invention medical treatment table overcomes the disadvantages of the prior art traction devices.

SUMMARY OF THE INVENTION

The general purpose of the present invention is a medical treatment table providing for mobility and comfort in treatment of a patient.

According to one embodiment of the present invention, there is provided a medical treatment table comprising a quadruped floor stand including an upward extending pedestal, a table pivotally mounted at the top of the pedestal, a half circumferential ring gear affixed to the underside of the table, a ring gear drive motor including an override crank engaged to the ring gear, parallel bars running perpendicular to the table at one end of the table, two motor means mounted adjacent to the bars, ankle-leg harnesses connected to the two motor means, a bar at the other end of the table, a wire adapted for sliding over the bar and connected between a cervical neck traction harness and a weight, a two-bar linkage pivotal stand connected to the other end of the table, and a control box connected between the ring gear motor, the two-motor means, and a power outlet whereby the table is capable of being tilted and angled with respect to the pedestal for inclination of the level of the table, for separation of the ankles and legs with respect to the body, and for traction of the bones of the body.

A significant aspect and feature of the present invention is a medical treatment table which provides mobility and comfort to the patient.

Another significant aspect and feature of the present invention is a medical treatment table for self use by the patient.

An object of the present invention is a medical treatment table for self use by a patient for medical treatment.

BRIEF DESCRIPTION OF THE DRAWINGS

Other objects and many of the attendant advantages of this invention will be readily appreciated as the same becomes better understood by reference to the following detailed description when considered in connection with the accompanying drawings, in which like reference numerals designate like parts throughout the figures thereof and wherein.

DETAILED DESCRIPTION OF PREFERRED EMBODIMENTS

Figure 1:
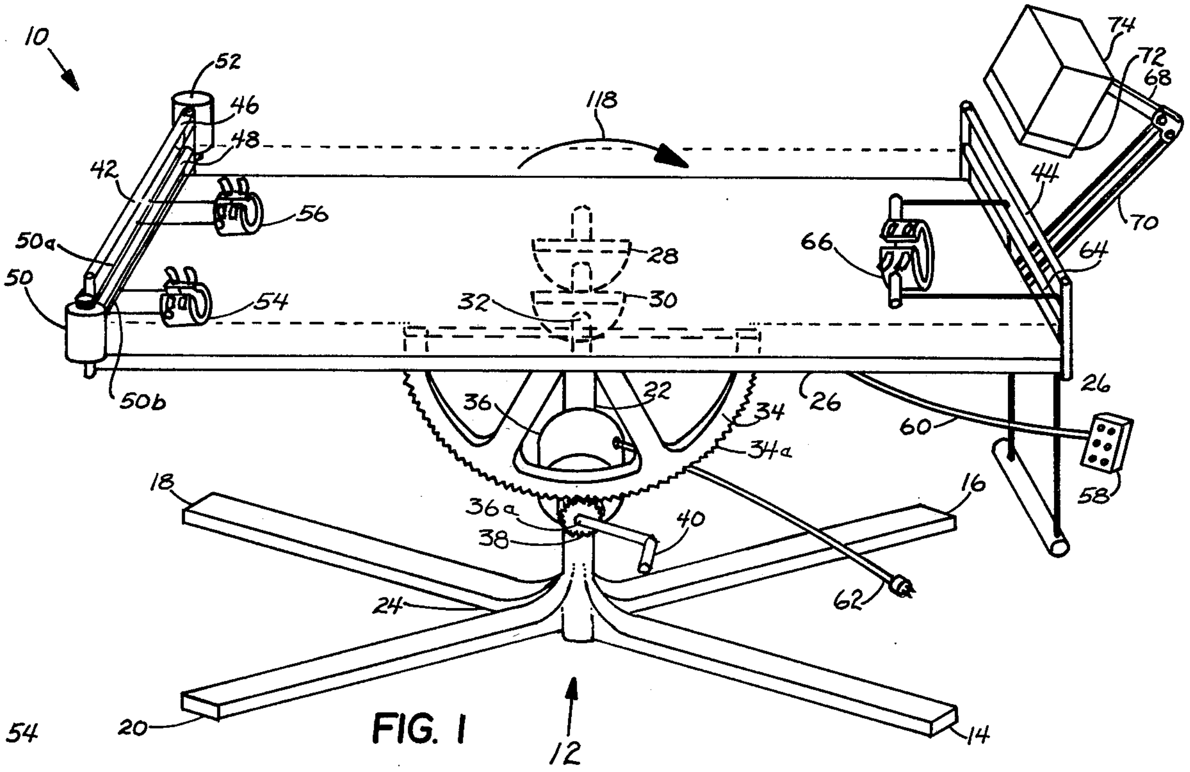
FIG. 1 illustrates a perspective plan view of a medical treatment table of the present invention.

FIG. 1, which illustrates a perspective plan of a medical treatment table 10, the present invention, shows a quadruped pedestal base 12 including four angularly outwardly extending pod legs 14–20 and a pedestal 22 extending upward from an apex 24 of the base 12. A medical treatment table 26 including centered pivot mounts 28 and 30 pivot about a pivot pin 32 secured between the pivot mounts 28 and 30 and through the pedestal 22. A half circumferential ring gear 34 having a plurality of teeth **34*a* affixes to the underside of the table 26 adjacent to the pivot mount 30. A motor 36 affixes to the pedestal 22 and includes a sprocket wheel 38 affixed to motor axis 36*a* which engages to the teeth 34*a* of the ring gear 34. A manual override crank 40 affixes to the motor axis 36*a* for manual operation in the event of power failure. Vertical upright end frames 42 and 44 affix to each end of the table 26, and contain a mattress 45 within the limits of the end frames 42 and 44. Horizontal bars 46 and 48 extend between the supports of the end frame 42. Motors 50 and 52 affix to each vertical member respectively of the end frame 42 and support endless wire or rope loops 50*a* and 52*a* running about each vertical member and adjacent to the bars 46 and 48 respectively. Ankle-leg harness 54 and 56 as later described in detail in FIG. 2 connects to the endless loops 50*a* and 52*a*. A motor control box 58 including a cord 60 connects between the motors 36, 50 and 52, and power cord 62. The motor control box includes a plurality of rocker switches for rotational control of the motors 36, 50 and 52 respectively. A horizontal bar 64 extends between the supports of the end frame 44 and supports the wire or cord of the cervical traction harness 66, as later described in detail in FIG. 3. A two-bar pivot linkage 68 and 70 connects between the edge of the table 26 and supports a stand 72 for medical equipment 74** or, alternatively, for entertainment equipment.

Figure 2:
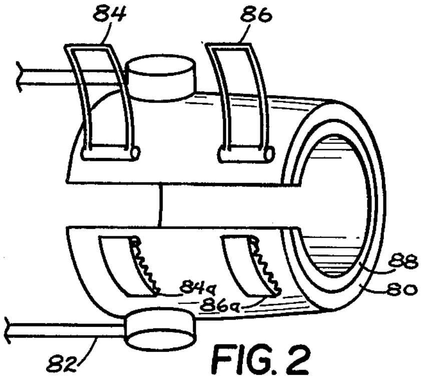
FIG. 2 illustrates an ankle-leg harness.

FIG. 2, which illustrates a fitted ankle-leg harness 80 as 54 or 56, shows a wire or cord **82*a* and 82*b* which connects between one of the endless loops 50*a* and 52*a* and the ankle-leg harness 80. The ankle-leg harness 80 includes a slit 83 running down a cylinder member for fitting over the ankle or leg of the patient, snap-on release fittings 84 and 86 for engagement with serated member 84*a* and 86*a* respectively, and soft padded inside linear 88** for patient comfort.

Figure 3:
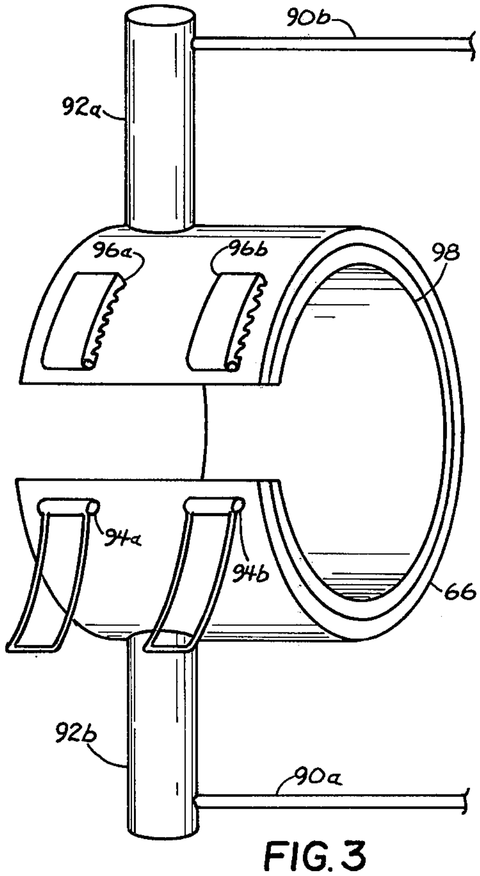
FIG. 3 illustrates a cervical neck harness.

FIG. 3, which illustrates a cervical neck harness 66, shows wire or cords **90*a* and 90*b* connected to extended apertures 92*a* and 92*b*, snap-on release fittings 94*a* and 94*b* for engagement with serated members 96*a* and 96*b* respectively, and soft padded inside linear 98 for patient comfort. A weight in the range of 1 to 10 pounds, preferably 5 pounds, connects to the end of cords 90*a* and 90*b* which ride over the bar 64**.

Figure 4:
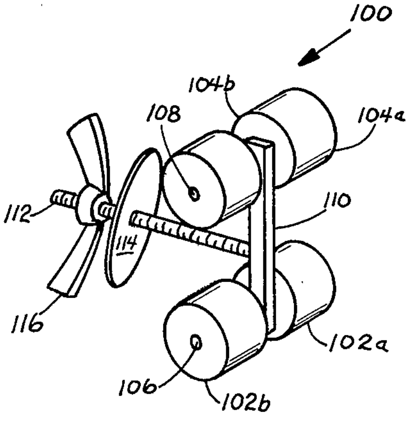
FIG. 4 illustrates an alternative embodiment of a foot-ankle-leg base.

FIG. 4, which illustrates an alternative embodiment of a foot-ankle-leg base 100 for clamping between the bars 46 and 48, includes two pairs of opposed rubber rollers **102*a*, 102*b*, 104*a* and 104*b*, joined by rod members 106 and 108; the rod members joined by bar 110, a perpendicular thread rod 112 including a washer 114 of large diameter and a large wing nut 116** respectively as illustrated.

PREFERRED MODES OF OPERATION

The operation of the medical treatment table 10 of FIG. 1 is controlled by motor control box 58 which regulates the angulation of the table 10 through the motor 36, and the degree of angular separation of the patient's legs through motors 50 and 52.

The patient's legs are secured in the ankle-leg harness 80 of FIG. 2, and the table 10 is tilted downward in the direction of the arrow 118 to provide traction as required for medical treatment of a predetermined condition. The cervical traction harness 66 of FIG. 3 can be secured to a patient's neck and weighted as predetermined with the cords 90 riding on the bar 64.

In the event motors 50 and 52 are not utilized, the foot-ankle base 100 can be utilized to secure cords 82 of the ankle-leg harnesses.

Various modifications can be made to the medical treatment table of the present invention without departing from the apparent scope thereof. The table can accommodate more than one person and can have more than one degree of freedom.

Having thus described the invention, what is claimed is:

1. Medical treatment table for treating predetermined medical conditions, comprising:

a. table including end frame supports and two centered pivot mounts;

b. half circumferential ring gear adjacent to one of said pivot mounts on the bottom of said table;

c. pedestal base including an upward extending pedestal, four pods extending angularly outward from said pedestal, and a pivot pin extending through a top portion of said pedestal and through said pivot mounts;

d. motor drive means including a sprocket at a base of said pedestal and engaged to said ring gear for angularly tilting said table;

e. control means for switching power to said motor means where said motor tilts said table for treating a patient; and, f. second motor means on each end of one of said end frames, pulleys anchored at each end of said second motor means, and an ankle-leg harness means connected to an endless loop about said pulleys whereby said motor means varies positioning of said endless loops about said pulley thereby varying distance of said ankle-leg harness with respect to each other.

2. Medical treatment table of claim 1 wherein said ankle-leg harness means comprises a cord connected between said endless loops and an ankle-leg harness, said ankle-leg harness including a slitted cylindrical member, snap-on release means across said slit, and padding means on interior of said member.

3. Medical treatment table of claim 1 further comprising two horizontal bars running between one end of said end frame, two ankle base means including rubber support means and wing nut means securing said rubber support means to said bar means, and ankle harness means connected to said rubber means whereby said rubber support means secures said ankle harness means to said end frame means.

4. Medical treatment table of claim 1 comprising a horizontal bar running across the other end of said end frame and a neck harness means including a weight cord suspended over said bar whereby said neck harness secures to a patient's head thereby providing predetermined traction.

5. Medical treatment table of claim 1 comprising a mattress on said table whereby said mattress provides for patient comfort.

6. Medical treatment table of claim 1 wherein said table is for treatment of scoliosis.

7. Medical treatment table of claim 1 wherein said table is for treatment of predetermined medical bone-related disorders.

8. Medical treatment table of claim 1 comprising a two-bar pivot linkage connected to end of said table opposite said second motor means and including a support means at an unconnected end for supporting electrical equipment.

9. Medical treatment table of claim 8 wherein said electrical equipment is medical equipment.

10. Medical treatment table of claim 8 wherein said electrical equipment is entertainment equipment.

* * * * *